United States Patent [19]  [11] 4,189,595
Sakoda et al. [45] Feb. 19, 1980

[54] [N-BENZYL-O-(2,6-DICHLOROANILINO)-PHENYL]ACETIC ACID DERIVATIVES

[75] Inventors: Ryozo Sakoda; Kazuo Nagano; Yumiko Ando, all of Funabashi; Genichi Tsuchihashi, Tama; Katsuyuki Ogura, Sagamihara, all of Japan

[73] Assignees: Nissan Chemical Industries, Ltd.; Sagami Chemical Research Center, both of Tokyo, Japan

[21] Appl. No.: 938,252

[22] Filed: Aug. 30, 1978

[30] Foreign Application Priority Data

Sep. 20, 1977 [JP] Japan .................................. 52/112210

[51] Int. Cl.² .................. C07C 153/11; C07C 101/48; C07C 101/50
[52] U.S. Cl. ................................. 560/47; 260/455 R; 562/457
[58] Field of Search .................... 260/455 R; 562/457; 560/47

[56] References Cited
U.S. PATENT DOCUMENTS 3,816,388  6/1974  Weaver et al. .................. 560/47
3,910,958 10/1975  Tsuchihashi et al. ........ 260/340.5 R Primary Examiner—Alan L. Rotman
Assistant Examiner—Robert C. Whittenbaugh
Attorney, Agent, or Firm—Oblon, Fisher, Spivak, McClelland & Maier

[57] ABSTRACT

Novel compounds of [N-benzyl-o-(2,6-dichloroanilino)-phenyl]acetic acid derivatives having the formula

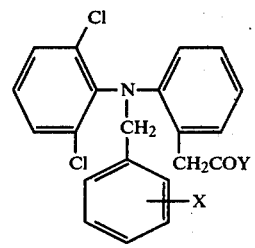

wherein X represents H, Cl, Br or a $C_1$–$C_4$ alkyl group and Y is OH, OR or SR and R represents a $C_1$–$C_4$ alkyl group.

13 Claims, No Drawings

[N-BENZYL-O-(2,6-DICHLOROANILINO)-PHENYL]ACETIC ACID DERIVATIVES

BACKGROUND OF THE INVENTION

The present invention relates to novel compounds of [N-benzyl-o-(2,6-dichloroanilino)phenyl]acetic acid derivatives.

It has been known that o-(2,6-dichloroanilino)-phenylacetic acid and salts thereof are important medicines having antiinflammatory and analgic effects in Experientia page 450 (1973) by P. J. Krupp, R. M. Gdynia, A. Sallmann, G. Wilhelmi, R. Ziel and R. Jaques.

It has been proposed to produce o-(2,6-dichloroanilino) phenyl acetic acid by the following processes.

(1) Hydrolysis of N-(2,6-dichlorophenyl)indolinone with base British (Pat. No. 1,139,332.

(2) Hydrolysis of o-(2,6-dichloranilino)benzyl cyanide with base British Pat. No. 1,139,332.

(3) Reaction of o-(2,6-dichloroanilino)acetophenone with sulfur and morpholine and hydrolysis of the resulting morpholide British Pat. No. 1,183,968.

In these processes, N-(2,6-dichlorophenyl)anthranilic acid is the starting material.

In the process (1), N-(2,6-dichlorophenyl)indolinone is produced by a reaction by chloroacetyl chloride with 2,6-dichlorodiphenylamine which is produced by a thermal decomposition of N-(2,6-dichlorophenyl)anthranilic acid.

In the process (2), o-(2,6-dichloroanilino)benzyl cyanide is produced by reducing N-(2,6-dichlorophenyl)anthranilic acid with lithium aluminum halide and converting the resulting o-(2,6-dichloroanilino)benzyl alcohol to a halide thereof and then, reacting sodium cyanide.

In the process (3), o-(2,6-dichloroanilino)acetophenone is produced from N-(2,6-dichlorophenyl)anthraniloyl chloride.

In these conventional processes, o-(2,6-dichloroanilino)phenylacetic acid is produced by complex steps from the starting material of N-(2,6-dichlorophenyl)anthranilic acid which is produced by the Ullmann reaction of 2,6-dichloroaniline with 2-halobenzoic acid or the reaction of 2,6-dichloro-1-bromobenzene with anthranilic acid in the presence of a copper type catalyst. However, the yield of the Ullmann reaction is unthinkably low to contaminate impurities and accordingly, the product obtained from N-(2,6-dichlorophenyl)anthranilic acid should be purified by expensive methods to use the product as a medicine.

SUMMARY OF THE INVENTION

It is an object of the present invention to provide novel compounds of [N-benzyl-o-(2,6-dichloroanilino)-phenyl]acetic acid derivatives in high purity.

It is another object of the present invention to use of the novel compounds of [N-benzyl-o-2,6-dichloroanilino)phenyl]acetic acid derivatives to produce o-(2,6-dichloroanilino)phenylacetic acid in high purity.

The novel compounds of [N-benzyl-o-2,6-dichloroanilino)phenyl]acetic acid derivatives is represented by the formula

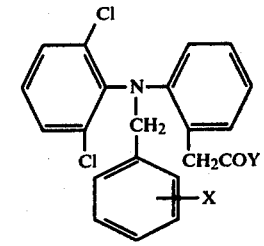

wherein X represents H, Cl, Br or a $C_1$-$C_4$ alkyl group and Y is OH, OR or SR and R represents a $C_1$-$C_4$ alkyl group.

DETAILED DESCRIPTION OF THE PREFERRED EMBODIMENTS

The novel compounds having the formula (I) include [N-benzyl-o-(2,6-dichloroanilino)phenyl]acetic acid, [N-halobenzyl-o-(2,6-dichloroanilino)phenyl]acetic acid, [N-$C_1$-$C_4$ alkylbenzyl-o-(2,6-dichloroanilino)-phenyl]acetic acid, $C_1$-$C_4$ alkyl[N-benzyl-o-(2,6-dichloroanilino)phenyl]acetate, $C_1$-$C_4$ alkyl[N-halobenzyl-o-(2,6-dichloroanilino)phenyl]acetate, $C_1$-$C_4$ alkyl[N-$C_1$-$C_4$ alkylbenzyl-o-(2,6-dichloroanilino)-phenyl]acetate, $C_1$-$C_4$ alkyl[N-benzyl-o-(2,6-dichloroanilino)phenyl]thioacetate, $C_1$-$C_4$ alkyl[N-halobenzyl-o-(2,6-dichloroanilino)phenyl]thioacetate, and $C_1$-$C_4$ alkyl[N-$C_1$-$C_4$ alkylbenzyl-o-(2,6-dichloroanilino)phenyl]thioacetate.

The novel compounds in the form of acetic acid have the formula

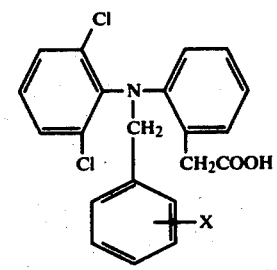

wherein X represents H, Cl, Br or a $C_1$-$C_4$ alkyl group.

The novel compounds in the form of acetic acid esters have the formul

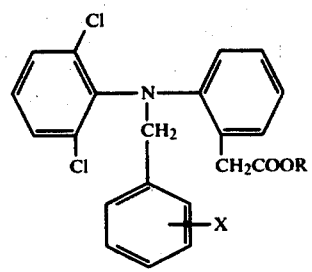

wherein X is defined above and R represents a $C_1$-$C_4$ alkyl group.

The novel compounds in the form of thioacetic acid esters have the formula

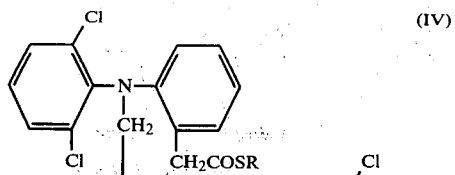

wherein X and R are defined above.

The novel compounds of [N-benzyl-o-(2,6-dichloroanilino)phenyl]acetic acid derivative (I) can be produced by reacting water or an alcohol in the presence of a mineral acid with the corresponding 1-[N-benzyl-o-(2,6-dichloroanilino)phenyl]-2-alkylsulfinyl-2-alkylthioethylene (V).

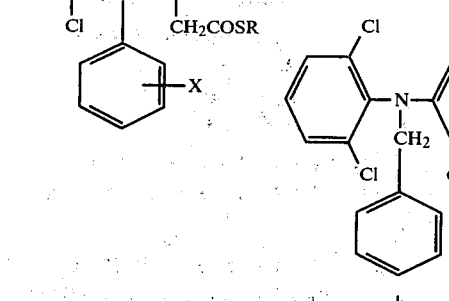

wherein X and R are defined above.

When the product is [N-benzyl-o-(2,6-dichloroanilino)phenyl]acetic acid water or thioacetic acid ester, the product can be easily converted to the corresponding [N-benzyl-o-(2,6-dichloroanilino)phenyl]acetic acid by hydrolyzing it with an acid or a base.

Typical example will be illustrated by the reaction formulae

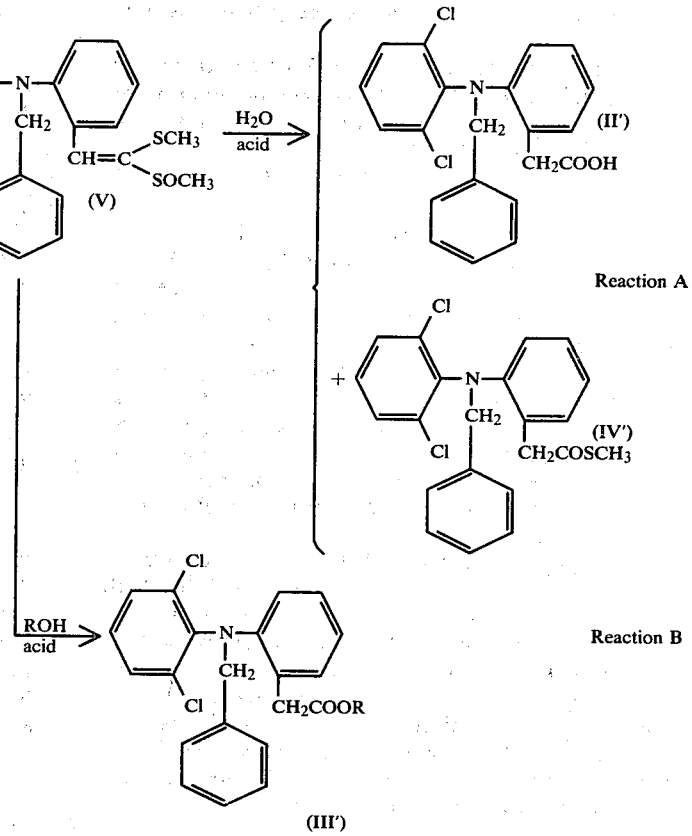

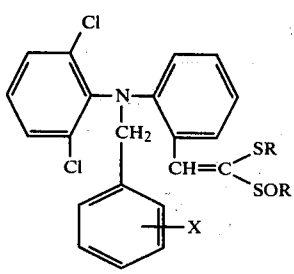

In Reaction A, 1-[N-benzyl-o-(2,6-dichloroanilino)phenyl]2-methylsulfinyl-2-methylthioethylene (V') is reacted with water in the presence of a mineral acid.

In the reaction, it is possible to use an aprotic solvent such as THF, dioxane, ethyleneglycol dimethyl ether etc. For example, the starting material (V') disappears by the reaction at 80° C. for 4 hours, and both [N-benzyl-o-(2,6-dichloroanilino)phenyl]acetic acid (II') and methyl [N-benzyl-o-(2,6-dichloroanilino)phenyl]thioacetate (IV') are obtained. The ratio of the compounds can be varied depending upon the conditions in the reaction and the yield of both products can be higher than 90%.

In Reaction B, 1-[N-benzyl-o-(2,6-dichloroanilino)phenyl]2-methylsulfinyl-2-methylthioethylene (V') is reacted with an alcohol in the presence of a mineral acid whereby [N-benzyl-o-(2,6-dichloroanilino)phenyl]acetic acid ester (III') is obtained.

When ethanol is used as the alcohol, the starting material (V') disappears by the reaction at 80° C. for 4 hours and almost stoichiometric amount of the product is produced.

The mineral acids can be hydrochloric acid, sulfuric acid and phosphoric acid and others and it is mostly preferable to use hydrohalogenic acid such as hydrochloric acid because the reaction performs smoothly.

The thioacetic acid ester (IV') or the acetic acid ester (III') can be easily hydrolyzed with a base or an acid to obtain [N-benzyl-o-(2,6-dichloroanilino)phenyl]acetic acid (II').

The alcohol can be methanol, ethanol, propanol or butanol. Excess alcohol can be used as a solvent. If necessary, the other solvent such as benzene, toluene, or THF can be used. The reaction can be performed at room temperature and the reaction can be promoted by heating it.

When a mixture of [N-benzyl-o-(2,6-dichloroanilino)-phenyl]acetic acid (II') and the thioacetic acid ester (IV') is obtained in the Reaction A, the mixture is treated with a base or an acid without separating them to hydrolyze the thioacetic acid ester (IV') whereby [N-benzyl-o-(2,6-dichloroanilino)phenyl]acetic acid (II') can be obtained in high yield.

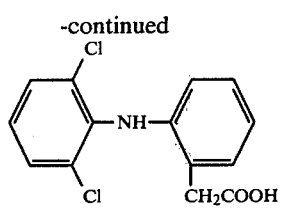

(VI')

The noble metal type catalyst can be Pd catalyst and Rh catalyst.

The Pd catalyst is preferably a catalyst supporting Pd on a carrier such as activated carbon, alumina, diatomaceous earth, silica gel, silica-alumina etc. It is mostly preferable to use Pd-activated carbon or Pd-alumina.

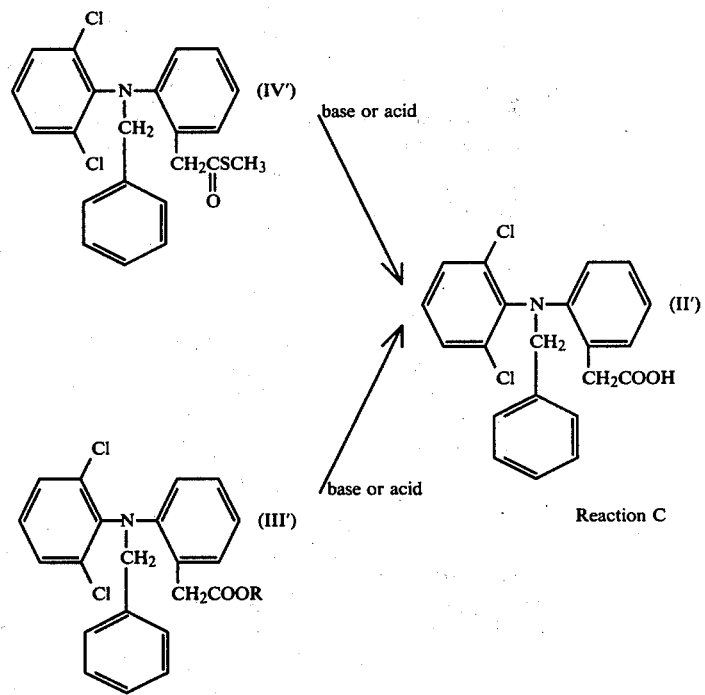

Reaction C

[N-benzyl-o-(2,6-dichloroanilino)phenyl]acetic acid (II') is easily converted to o-(2,6-dichloroanilino)-phenylacetic acid (VI') having high purity in high yield by reacting hydrogen in the presence of a noble metal type catalyst in Reaction D.

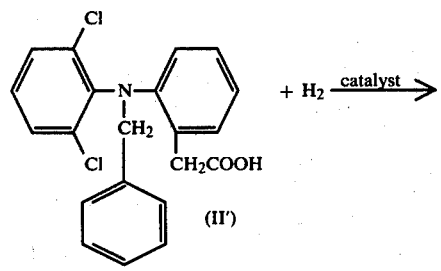

The catalyst is usually used in a range 0.1 to 100 wt. % preferably 1 to 40 wt. % to the starting material (II').

The dechlorination is caused at higher than 80° C. when only Pd catalyst is used. When 1 to 40 wt. % of 5% Rh-carbon catalyst is added to the Pd-catalyst or 1 to 20 wt. parts of metal chloride such as palladium chloride or iron chloride is added, the dechlorination can be prevented. In the latter case, the selectivity is improved but the reaction velocity is decreased. It is mostly preferable to use Pd-catalyst with palladium chloride since the decrease of the reaction velocity is slight.

The solvents used in the reaction can be aromatic and aliphatic hydrocarbons and other solvents such as benzene, toluene, xylene, tetralin, chlorobenzene, n-octane, n-decane, decaline, monoglyme and diglyme.

In the hydrogenolysis, a dechlorination is slightly found at higher than 80° C. when the above-mentioned solvent is used. However, the dechlorination is significantly prevented by adding more than 5 wt. % of dichlorobenzene or by carrying out the reaction in dichlorobenzene. Accordingly, it is mostly preferable to use a solvent of xylene or toluene containing about 5 wt. % or more of dichlorobenzene.

The amount of the solvent is usually 2 to 30 wt. parts to 1 parts of the starting material. When it is too much, the volumetric efficiency of the reactor is decreased and the reaction time is prolonged. The amount of the solvent is preferably in a range of 3 to 8 wt. parts to 1 wt. part of the starting material.

The reaction temperature is usually in a range of 30° to 170° C. preferably 60° to 130° C. and the reaction time is usually in a range of 30 minutes to 10 hours preferably 30 minutes to 3 hours.

The hydrogen pressure in the hydrogenolysis is usually in a range of 1 to 100 atm., preferably 1 to 40 atm., especially atmospheric pressure.

By this hydrogenolysis, o-(2,6-dichloroanilino)-phenylacetic acid (VI′) having high purity which is useful medicine can be obtained in high yield by a simple process. That is, o-(2,6-dichloroanilino)phenylacetic acid (VI′) can be obtained as pure colorless crystals without a complicated purification step such as recrystallization etc.

When o-(2,6-dichloroanilino)phenylacetic acid (VI′) is neutralized with an alkali metal hydroxide such as sodium hydroxide, alkali metal salts such as sodium o-(2,6-dichloroanilino)phenyl acetate in pure colorless flaky form can be obtained.

1-[N-benzyl-o-(2,6-dichloroanilino)phenyl]-2-alkyl-sulfinyl-2-alkylthioethylene (V) can be produced by reacting N-(2,6-dichlorophenyl) anthranilaldehyde having the formula

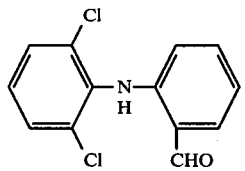

with a benzyl halide having the formula

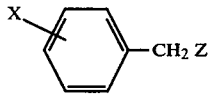

wherein Z is Br or Cl and X is defined above, in the presence of an alkali metal hydride in an aprotic polar solvent to produce N-(2,6-dichlorophenyl)-N-benzylanthranilaldehyde, followed by the reaction of the resulting aldehyde with formaldehyde dialkyl mercaptal S-oxide having the formula

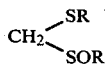

wherein R is a lower alkyl group.

In the reaction, it is necessary to separate the intermediate of N-(2,6-dichlorophenyl)-N-benzyl anthranilaldehyde.

The aprotic polar solvents include DMF, DMSO, tetramethyl urea, THF etc. It is possible to mix a hydrocarbon such as benzene, toluene, xylene with the aprotic polar solvent.

The alkali metal hydrides can be sodium hydride, potassium hydride and lithium hydride and sodium hydride is mostly preferable from the viewpoint of economy and reactivity.

The amount of alkali metal hydride is about 2 equivalents to the starting material and excess alkali metal hydride can be used. The alkali metal hydride can be added at once but it is preferably added for several times whereby the object compound is obtained in higher yield.

The reaction is performed at 0° to 70° C. but it is preferable to react them at 0° to 40° C. from the viewpoint of easy operation.

1-[N-benzyl-o-(2,6-dichloroanilino)-phenyl]-2-alkyl-sulfinyl-2-alkylthioethylene derivative (V) can be also produced by reacting N-(2,6-dichlorophenyl) anthranilaldehyde with the formaldehyde dialkyl mercaptal S-oxide having the formula

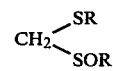

in the presence of an alkali metal hydride in a solvent and then, reacting the resulting 1-[o-(2,6-dichloroanilino)phenyl]-2-alkylsulfinyl-2-alkylthioethylene with a benzyl halide having the formula

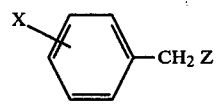

in the presence of an alkali metal hydride in a solvent.

The solvent can be the same with the aprotic polar solvent if necessary with hydrocarbons.

The present invention will be further illustrated by certain examples.

REFERENCE 1

In 133 g of dimethylformamide (DMF), 22 g of sodium hydride (55%; oil dispersion) was dispersed and the dispersion was cooled to lower than 25° C., and a solution of 133 g of N-(2,6-dichlorophenyl)anthranilaldehyde in 266 g of DMF was added dropwise during 30 minutes to the dispersion and then 85.5 g of benzyl bromide was added dropwise during 30 minutes and the mixture was stirred at 20° C. for 1 hour and 22 g of sodium hydride (55%; oil dispersion) was added and then, 62 g of formaldehyde dimethyl mercaptal S-oxide was added dropwise during 1 hour at the reaction temperature of lower than 25° C. The precipitate was filtered and washed with methanol and water and dried under a reduced pressure to obtain 210.2 g of 1-[N-benzyl-o-(2,6-dichloroanilino)phenyl]2-methylsulfinyl-2-methylthioethylene as pale yellow crystals. Melting point 194° to 196° C. (benzene)

IR (KBr) 1593, 1482, 1448, 1430, 1325, 1230, 1220, 1050, 784, 740, 772 cm$^{-1}$

NMR (CDCl$_3$) δ1.95 s (3H), 2.46 s (3H), 4.84 s (2H) 6.7–7.7 m (13H)

Elementary analysis as $C_{23}H_{21}NOS_2Cl_2$: Found (%): C, 59.73; H, 4.58; N, 3.03; S, 13.87. Calculated (%): C, 59.92; H, 4.53; N, 3.05; S, 13.88.

REFERENCE 2

In 25 ml of DMF, 3.8 g (0.010 mole) of 1-[o-(2,6-dichloroanilino)phenyl]-2-methylsulfinyl-2-methylthioethylene was dissolved and 0.98 g (0.022 mole) of sodium hydride (55%; oil dispersion) was added at 20° to 30° C. and the mixture was stirred at 80° C. for 1 hour and cooled to 20° C. and 44 g (0.026 mole) of benzyl bromide was further added and the mixture was stirred at room temperature (20° to 30° C.) for 12 hours and the reaction mixture was poured into a large amount of water to precipitate yellow crystals and the resulting crystals were filtered and dried under a reduced pressure and further recrystallized from benzene to obtain 4.5 g of 1-[N-benzyl-o-(2,6-dichloroanilino)phenyl]-2-methylsulfinyl-2-methylthioethylene as pale yellow crystals. Yield: 98%

REFERENCE 3

In 6 ml of dry DMF, 0.72 g of sodium hydride (55%; oil dispersion) was dispersed and then, 0.67 g of formaldehyde dimethyl mercaptal S-oxide was added to the dispersion under cooling with ice-water and then, 1.33 g of N-2,6-dichlorophenylanthranilaldehyde was slowly added to the mixture and the temperature was gradually elevated to the room temperature. The mixture was kept at the room temperature for 1 night and then, 2.6 g of benzyl bromide was added dropwise at the room temperature and the mixture was stirred for 3 hours and poured into a large amount of water to precipitate a solid component and the solid component was filtered, washed with methanol and dried to obtain 2.3 g of pale yellow crystals.

The melting point, IR and NMR of the pale yellow crystals were identical with those of the product of Reference 1. Yield: 100%

EXAMPLE 1

In 26 ml of 1,2-dimethoxyethane, 1.2 g (0.0026 mole) of 1-[N-benzyl-o-(2,6-dichloroanilino)phenyl]-2-methylsulfinyl-2-methylthioethylene was dissolved and then, 13 ml of conc. HCl was added and the mixture was stirred at 80° C. for 4 hours. The reaction mixture was cooled and 80 ml of methylene chloride and 10 ml of water were added to extract the reaction product and the separated water phase was further mixed with 70 ml of methylene chloride to extract the reaction product. Both of methylene chloride phases were combined, dried over anhydrous sodium sulfate, and then concentrated under reduced pressure. The residue was separated by a column chromatography (silica gel: Wako gel Q-23 manufactured by Wako Junyaku and developing solvent:n-hexane:acetone=2:1) to obtain 0.14 g (yield: 14%) of N-benzyl-o-(2,6-dichloroanilino)phenyl acetic acid and 0.88 g (yield: 81%) of methyl N-benzyl-o-(2,6-dichloroanilino)phenylthioacetate.

N-benzyl-o-(2,6-dichloroanilino)phenyl acetic acid.
Melting point 174° to 176° C. (ether-petroleum ether)
IR (KBr) 3060-2400, 1705, 1600, 1435, 1220, 790, 770, 750, 725, 690 cm$^{-1}$
NMR (CDCl$_3$) $\delta$3.5 s (2H), 4.85 s (2H), 6.7–7.5 m (12H)
Elementary analysis as $C_{27}H_{17}NO_2Cl_2$: Found (%): C, 65.12; H, 4.36; N, 3.56. Calculated (%): C, 65.30; H, 4.44; N, 3.63.

Methyl N-benzyl-o-(2,6-dichloroanilino)phenylthioacetate.
Melting point 128° to 129° C. (cyclohexane)
IR (KBr) 2800, 1688, 1600, 1490, 1430, 1225, 790, 775, 743, 720, 690 cm$^{-1}$
NMR (CDCl$_3$) $\delta$2.10 s (3H), 3.71 s (2H), 4.90 s (2H), 6.8–7.7 m (12H)

Elementary analysis as $C_{22}H_{19}NCl_2OS$: Found (%): C, 63.52; H, 4.49; N, 3.34. Calculated (%): C, 63.46; H, 4.60; N, 3.36.

EXAMPLE 2

In a mixture of 30 ml of ethanol and 22 ml of benzene, 9.0 g (0.019 mole) of 1-[N-benzyl-o-(2,6-dichloroanilino)phenyl]-2-methylsulfinyl-2-methylthioethylene was dissolved and 45 ml of ethanol saturated with hydrogen chloride was added and the mixture was refluxed for 4 hours. The reaction mixture was concentrated under reduced pressure and the residue was separated by a column chromatography (silica gel: Wakogel Q-23 manufactured by Wako Junyaku; developing solvent: benzene) to obtain 7.9 g of ethyl N-benzyl-o-(2,6-dichloroanilino)phenylacetate as colorless crystals. Yield: 97%

Melting point 100° to 103.5° C.
IR (KBr) 1728, 1595, 1438, 1427, 1200, 1140, 780, 770, 735, 720, 685 cm$^{-1}$
NMR (CDCl$_3$) $\delta$1.11–1.33 t (3H), 3.42 s (2H), 3.75–4.15 q (2H), 4.85 s (2H), 6.7–7.6 m (12H)

EXAMPLE 3

In 4 ml of 1,2-dimethoxyethane, 0.25 g (0.00060 mole) of methyl N-benzyl-o-(2,6-dichloroanilino)phenyl thioacetate was dissolved and 3 ml of 1 N-NaOH aq. sol. was added and the mixture was refluxed for 6 hours and then, it was cooled and 20 ml of ether was added and the reaction product was extracted 2 times with 1 N-NaOH aq. sol. The pH of the water phase was adjusted to 2.0 and the reaction product was extracted with 30 ml of ether. The ether phase was dried with anhydrous sodium sulfate and concentrated under reduced pressure. The residue was recrystallized from ether-petroleum ether to obtain 0.15 g of N-benzyl-o-(2,6-dichloroanilino)phenylacetic acid as colorless crystals.

The melting point, IR and NMR were identical with those of Example 1.

EXAMPLE 4

In a mixture of 50 ml of ethanol and 30 ml of benzene, 7.0 g (0.017 mole) of ethyl N-benzyl-o-(2,6-dichloroanilino)phenylacetate was dissolved and 31 ml of 2 N-NaOH aq. sol. was added and the mixture was stirred at about 80° C. for 9 hours. The reaction mixture was concentrated under reduced pressure and 70 ml of ether was added to the residue and the reaction product was extracted with 2 N-NaOH aq. sol. The pH of the water phase was adjusted with a dilute hydrochloric acid to 2.0 and the precipitate was extracted with ether and the ether phase was dried over anhydrous sodium sulfate and concentrated under a reduced pressure. The reaction product was recrystallized and 5.1 g of N-benzyl-o-(2,6-dichloroanilino)phenyl acetic acid was obtained as colorless crystals. Yield: 78%

The melting point, IR and NMR were identical with those of Example 1.

EXAMPLE 5

To a mixture of 40 ml of benzene and 70 ml of methanol containing 4 g of hydrogen chloride, 15.0 g of 1-[N-benzyl-o-(2,6-dichloroanilino)phenyl]-21 -methylsulfinyl-2-methylthioethylene was added and the mixture was refluxed for 3.5 hours under stirring. The solvent was removed under a reduced pressure and the residue was recrystallized from a mixture of benzene-methanol to obtain 9.4 g of methyl N-benzyl-o-(2,6- dichloroanilino)phenylacetate as colorless crystals. Yield: 72%

EXAMPLE 6

The mixture of 4.3 g of methyl N-(p-methylbenzyl)-o-(2,6-dichloroanilino)phenylacetate, 8 ml of benzene, 5 ml of ethanol, 8 ml of water and 2.5 g of 98% sodium hydroxide was refluxed for 8 hours under thoroughly stirring. After cooling the reaction mixture, 10% HCl aq. sol. was added to adjust pH 2 to 3 and 30 ml of ether was added and the ether phase was separated. The ether solution was dried over anhydrous sodium sulfate and the solvent was distilled off and the residue was recrystallized from ether-hexane to obtain 3.4 g of N-(p-methylbenzyl)-o-(2,6-dichloroanilino)phenylacetic acid as colorless crystals. Yield: 85%

Melting point 154° to 158° C. (ether-hexane)
IR (KBr) 3100–2500, 1710, 1600, 1492, 1456, 1430, 1410, 1217, 810, 780, 750, 740 cm$^{-1}$
NMR (CDCl$_3$) δ2.19 s (3H), 3.32 s (2H), 4.75 s (2H), 6.8–7.5 m (11H)

EXAMPLE 7

In a mixture of 40 ml of benzene and 50 ml of methanol containing 6 g of hydrogen chloride, 9.5 g of 1-[N-(p-methylbenzyl)-o-(2,6-dichloroanilino)phenyl]-2-methylsulfinyl-2-methylthioethylene was added and the mixture was refluxed for 5 hours under stirring. The solvent was distilled off under reduced pressure and the residue was recrystallized from benzene-methanol to obtain 4.7 g of methyl N-(p-methylbenzyl)-o-(2,6-dichloroanilino)phenylacetate as colorless crystals. Yield: 57%

Melting point 113° to 114° C. (benzene-methanol)
IR (KBr) 1740, 1600, 1495, 1460, 1428, 1205, 1150, 808, 786, 774, 748 cm$^{-1}$
NMR (CDCl$_3$) δ2.23 s (3H), 3.42 s (3H), 3.45 s (2H), 4.83 s (2H), 6.8–7.4 m (11H)

REFERENCE 4

To 10 ml of tetrahydronaphthalene, 0.78 g (0.0020 mole) of N-benzyl-o-(2,6-dichloroanilino)phenylacetic acid and 0.60 g of 5% Pd-alumina were added and the reaction was carried out at 145° to 155° C. for 2 hours under 40 atom of hydrogen pressure. The reaction mixture was filtered to remove Pd-alumina, and washed with THF and concentrated under a reduced pressure. The residue was separated by a thin layer chromatography (silica gel and developing solvent: hexane:acetone=2:1) to obtain 0.48 g of pale yellow viscous oily product. The oily product was kept for one day to crystallize. The product was confirmed to be o-(2,6-dichloroanilino)phenyl acetic acid from the following metling point, IR and NMR. Yield: 80%

Melting point 159° to 162° C. (chloroform)
IR (KBr) 3320, 3050–2400, 1690, 1505, 1450, 1300, 930, 760, 733 cm$^{-1}$
NMR (CDCl$_3$) δ3.82 s (2H), 6.5–7.4 m (8H)
Mass spectrometry (20 ev): m/e 297 (M$^+$+2, 46.7%), 296 (M$^+$+1, 12.1%), 295 (M$^+$, 71.2%), 279 (7.7%), 277 (11.4%), 244 (14.6%), 243 (7.7%), 242 (43.3%), 216 (36.7%), 215 (26.7%), 214 (base peak)

REFERENCE 5

In an autoclave, 55 ml of toluene, 4 ml of o-dichlorobenzene, 10.0 g of N-benzyl-o-(2,6-dichloroanilino)-phenylacetic acid and 2.0 g of 5% Pd-alumina were charged and it was purged with hydrogen gas and hydrogen gas was fed at 70° to 75° C. under a pressure of 10 to 20 cm H$_2$O for 1.5 hours. The reaction mixture at the same temperature was filtered to remove 5% Pd-alumina and catalyst was washed with 35 ml of THF. The filtrate and the washing were combined and THF and toluene were distilled off. The residue was admixed with 200 ml of n-hexane and cooled to obtain 7.0 g of o-(2,6-dichloroanilino)phenylacetic acid as colorless crystals. Yield: 91.2%

What is claimed is:

1. A compound of the formula

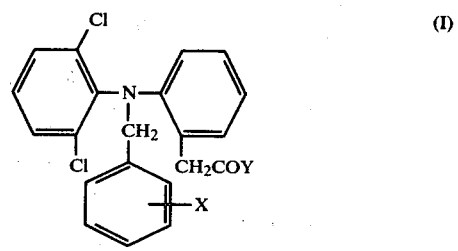

wherein X represents H, Cl, Br or a C$_1$–C$_4$ alkyl group and Y is OH, OR or SR and R represents a C$_1$–C$_4$ alkyl group.

2. A compound according to claim 1 wherein Y is OH, having the formula

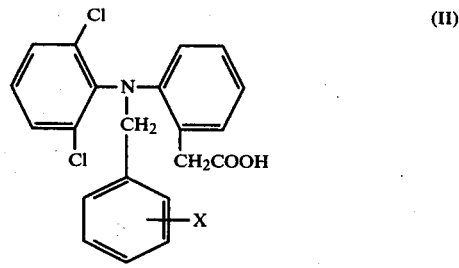

wherein X represents H, Cl, Br or a C$_1$–C$_4$ alkyl group.

3. A compound according to claim 1 wherein Y is OR, having the formula

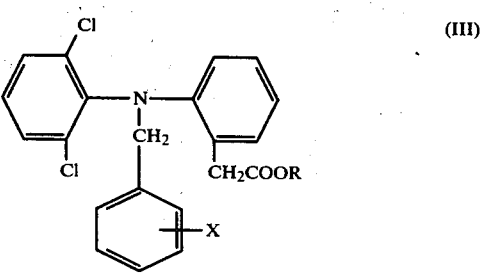

wherein X represents H, Cl, Br or a C$_1$–C$_4$ alkyl group and R represents a C$_1$–C$_4$ alkyl group.

4. A compound according to claim 1 wherein Y is SR, having the formula

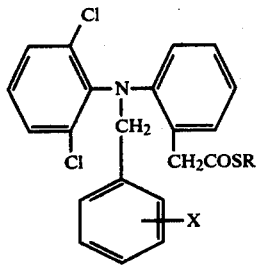

(IV)

wherein X represents H, Cl, Br or a $C_1$–$C_4$ alkyl group and R represents a $C_1$–$C_4$ alkyl group.

5. [N-benzyl-o-(2,6-dichloroanilino)phenyl]acetic acid.

6. [N-halobenzyl-o-(2,6-dichloroanilino)phenyl]acetic acid.

7. [N-$C_1$–$C_4$ alkylbenzyl-o-(2,6-dichloroanilino)phenyl]acetic acid.

8. $C_1$–$C_4$ alkyl[N-benzyl-o-(2,6-dichloroanilino)phenyl]acetate.

9. $C_1$–$C_4$ alkyl[N-halobenzyl-o-(2,6-dichloroanilino)phenyl]acetate.

10. $C_1$–$C_4$ alkyl[N-$C_1$–$C_4$ alkylbenzyl-o-(2,6-dichloroanilino)phenyl]acetate.

11. $C_1$–$C_4$ alkyl[N-benzyl-o-(2,6-dichloroanilino)phenyl]thioacetate.

12. $C_1$–$C_4$ alkyl[N-halobenzyl-o-(2,6-dichloroanilino)phenyl]thioacetate.

13. $C_1$–$C_4$ alkyl[N-$C_1$–$C_4$ alkylbenzyl-o-(2,6-dichloroanilino)phenyl]thioacetate.

* * * * *